United States Patent
Follmer et al.

[11] Patent Number: 5,827,242
[45] Date of Patent: Oct. 27, 1998

[54] REINFORCED CATHETER BODY AND METHOD FOR ITS FABRICATION

[75] Inventors: Brett A. Follmer, Santa Clara; William S. Tremulis, Redwood City, both of Calif.

[73] Assignee: Medtronic, Inc., Minneapolis, Minn.

[21] Appl. No.: 669,256

[22] Filed: Jun. 21, 1996

[51] Int. Cl.$^6$ .................................................. A61M 25/00
[52] U.S. Cl. ........................................ 604/282; 123/129
[58] Field of Search .................................. 604/264, 280, 604/282; 138/123, 129

[56] References Cited

U.S. PATENT DOCUMENTS

| | | | |
|---|---|---|---|
| 4,516,972 | 5/1985 | Samson | 604/282 |
| 4,596,563 | 6/1986 | Pande | 604/264 |
| 4,737,153 | 4/1988 | Shimamura et al. | 604/282 |
| 5,019,057 | 5/1991 | Truckai | 604/282 |
| 5,254,107 | 10/1993 | Soltesz | 604/282 |
| 5,279,596 | 1/1994 | Castaneda et al. | 604/282 |
| 5,454,795 | 10/1995 | Samson | 604/282 |
| 5,496,294 | 3/1996 | Hergenrother et al. | 604/282 |
| B2 4,739,768 | 10/1995 | Engelson | 128/658 |

OTHER PUBLICATIONS

Durometer Conversions, "Polyurethanes, The Bridge Between Silicone Rubbers and Plastics", one sheet.

*Primary Examiner*—Corrine M. McDermott
*Attorney, Agent, or Firm*—Townsend and Townsend and Crew LLP

[57] ABSTRACT

A catheter comprises a tubular body wherein at least a portion of the tubular body includes a helical reinforcement element. Both the tubular body and the helical reinforcement element are composed of polymeric materials, and the reinforcement element is fused to the material of the tubular body by applying heat and radially constrictive pressure. In this way, a helical reinforcement element providing significant hoop strength can be embedded within the tubular body with decreased risk of delamination. Optionally, an axial reinforcement element may be embedded within the tubular body between the helical reinforcement element and an outer portion of the tubular body matrix.

46 Claims, 2 Drawing Sheets

REINFORCED CATHETER BODY AND METHOD FOR ITS FABRICATION

This application is related to the following copending U.S. patent applications: Ser. No. 08/534,089, are filed on Sep. 26, 1995, which was a continuation of Ser. No. 08/151,320, filed on Nov. 12, 1993, now abandoned; Ser. No. 08/344,183, filed on Nov. 23, 1994; Ser. No. 08/562,565, filed on Nov. 24, 1995, which was a continuation in part of Ser. Nos. 08/344,183; 08/399,677, filed on Mar. 7, 1995; and Ser. No. 08/667,011 (filed on the same date of the present application). The full disclosures of each of these applications are incorporated herein by reference.

BACKGROUND OF THE INVENTION

1. Field of the Invention

The present invention relates generally to medical catheters and methods for their fabrication. More particularly the present invention relates to the design and construction of highly flexible tubular catheter bodies having circumferential and/or axial reinforcement.

Medical catheters exist for a wide variety of purposes, including diagnosis, interventional therapy, drainage, perfusion, and the like. Catheters for each of these purposes can be introduced to numerous target sites within a patient's body by guiding the catheter to the target site in some manner. For vascular access, the catheters may be positioned with or without the aid of a separate guidewire. When guidewires are not used, a least a distal portioned catheter may be formed from material which is sufficiently flexible and supple so that it may follow blood flow. Such catheters are commonly referred to as flow-directed catheters.

Of particularly interest to the present invention, small diameter tubular access catheters are presently being used for diagnostic and interventional neurological procedures, such as the imaging and treatment of aneurysms, tumors, arteriovenous malformations/fistulas and the like. Use in the neurological vascular places a number of requirements on such catheters. A primary requirement is size. The blood vessels in the brain are frequently several millimeters or less in diameter, and useful catheters must be as small as 1 French (1 French; 0.33 mm) or below. In addition to small size, the brain vasculature is highly tortuous and requires that at least a distal portion of the catheters be very flexible to accommodate such tortuosity. Flexibility and suppleness is a particular requirement of flow-directed catheters being used in the neurological vasculature. Such flexibility must be achieved, however, without excessive loss of column strength, tensile strength, and/or hoop strength.

Heretofore, a variety of reinforcement designs have been proposed for enhancing column strength, tensile strength, and/or hoop strength in flexible medical catheters. In particular, a variety of braid layers, helical wires, helical ribbons, and the like, have been incorporated into the walls of tubular catheters in order to enhance strength while retaining flexibility. Helical reinforcement elements have been particularly successful at providing enhanced hoop strength without substantial loss of flexibility.

While generally successful, catheters comprising prior helical support elements have suffered from certain drawbacks. In particular, most helical elements have been formed from a metal wire or ribbon which is embedded into the polymeric wall of the tubular catheter body. There is a tendency for such metal elements to separate or delaminate from the surrounding polymeric matrix. This is a particular problem in catheter bodies having very thin walls where metal coils can more readily separate from the surrounding polymeric matrix. Moreover, while they are highly effective in increasing hoop strength, helical support elements are less effective in enhancing tensile strength. Helices by their very nature, permit axial elongation in a manner analogous to a coil spring.

For these reasons, it would be desirable to provide flexible catheters and tubular catheter bodies having improved strength characteristics, including hoop strength, column strength, and tensile strength. In particular, it would be desirable to provide such improved strength characteristics without excessive or significant loss of flexibility. Catheters having such improved characteristics should be useful for a wide variety of medical applications, particularly including neurological and other vascular uses which require small diameter catheters e.g. having a diameter of 6 French and below, often 3 French and below, with wall thicknesses of 0.25 mm and below. The catheter structures should be useful to form the entire length of a catheter, or only a portion thereof, such as a distal portion. For catheters comprising a helical reinforcement element, the tendency for delamination should be reduced or eliminated. For other catheters, the tensile strength should be enhanced without significant increase in wall thickness or decrease in flexibility. At least some of these objectives will be addressed by various embodiments of the invention described below.

2. Description of the Background Art

A small diameter catheter intended for introduction into the neurological vasculature and having a metal coil embedded in about 2.5 cm of the its distal tip is sold by Medtronic Micro Interventional System, Inc., a subsidiary of the assignee of the present application. U.S. Pat. No. 4,739,768, describes a small diameter catheter having a distal end free from reinforcement. U.S. Pat. No. 4,516,972 describes a guide catheter having a pair of counter-wound helical Kevlar® ribbons reinforcing the body. The reinforcement ribbons are sandwiched between inner and outer tubular layers by heating a shrink wrap tube thereover. A separate bonding agent is used to attach the reinforcing ribbons to the tubular layers. U.S. Pat. No. 4,596,563 describes a catheter having a fuseless distal tip. Catheters having helical coils and other reinforcing layers are described in U.S. Pat. Nos. 5,496,294, 5,454,795; 5,279,596; and 5,254,107.

SUMMARY OF THE INVENTION

Catheters in accordance with the present invention comprise a tubular catheter body having at least a portion or axially segment thereof composed of a soft polymeric material. Usually, but not necessarily, the soft polymeric portion will be disposed at or near a distal end of the catheter body, and at least the soft polymeric portion or segment will be reinforced to enhance hoop and/or tensile strength. The reinforcement structures and methods of the present invention will result in little or no loss of flexibility and will have very little tendency to separate or delaminate from the polymeric matrix of the tubular catheter body. The present invention further provides methods for fabricating such catheters so that the reinforcement layers are properly incorporated therein.

In a first aspect of the present invention, a catheter comprises a tubular body wherein at least a portion of the tubular body includes a helical reinforcement element. The helical reinforcement element is composed of a first polymeric material and is embedded within a tubular matrix composed of a second polymeric material which is softer than the first polymeric material. The polymeric materials and fabrication conditions will be selected so that the reinforcement element is fused to the polymeric matrix so that the risk of delamination is greatly reduced or eliminated.

In a preferred embodiment, the first polymeric material has a hardness in the range from 40 D to 80 D and the second polymeric material has a hardness in the range from 20 A to 50 D. Usually, the first and second polymeric materials will be the same polymer, but will have different hardnesses in the ranges just set forth. In the exemplary embodiment, both the first polymeric material and the second polymeric material will be polyamide polyether block copolymers, with the first polymeric material of the reinforcement element having a hardness in the range from 40 D to 72 D and the second polymeric material of the tubular matrix having a hardness in the range from 25 D to 40 D.

In particularly preferred embodiments, the reinforced portions of the tubular body will be very thin, typically having thicknesses in the range from 0.05 mm to 0.35 mm, preferably from 0.1 mm to 0.25 mm. In such cases, it is further preferred that the wall structure will be free from other layers and components, i.e. it will consist essentially of just the reinforcement element and the tubular matrix. Usually, the reinforcement element will be disposed adjacent to an inner surface of the tubular wall, but the inner wall will remain smooth. Optionally, the inner tubular wall may be coated with a lubricious material such as a hydrophilic coating.

The helical reinforcement element may have any cross-sectional shape, but will usually be either circular, oval, or rectangular (i.e. a ribbon). Helical reinforcement elements having a circular cross-sectional will usually have a diameter in the range from 0.02 mm to 0.3 mm, while those having rectangular cross sections will have a width in the range from 0.05 mm to 0.5 mm and a thickness in the range from 0.025 mm to 0.15 mm.

The portion of the tubular body comprising the helical reinforcement element will usually have a small diameter, typically having an outer diameter in the range from 0.3 mm to 2 mm, preferably from 0.3 mm to 1 mm, and an inner diameter in the range from 0.2 mm to 1.5 mm, preferably from 0.2 mm to 0.8 mm. The length of the catheter will typically be from 40 cm to 200 cm, preferably from 60 cm to 150 cm, while the length of the reinforced portion (when less than the entire length of the catheter) will be in the range from 2 cm to 50 cm, typically from 5 cm to 30 cm. In order to retain flexibility, successive turns of the helical reinforcement element will be spaced apart from each other, typically by a distance in the range from 0.025 mm to 1 mm, preferably from 0.05 mm to 0.25 mm and the reinforcement element will typically have a pitch in the range from 10 turns/cm to 400 turns/cm, preferably from 80 turns/cm to 200 turns/cm. In the most common embodiments, the tubular body of the catheter will have a proximal end, a distal end, and at least one additional portion free from the helical reinforcement element (but optionally containing other reinforcement components), usually being a proximal portion which is more rigid than the helically reinforced portion.

In a second aspect of the present invention, catheters will comprise a tubular body wherein at least a portion of the tubular body includes a tubular matrix composed of a soft polymeric material having a hardness less than 55 D and a reinforcement element disposed axially within said portion. The reinforcement element will have a high tensile strength relative to the soft polymeric material. Usually, the axially reinforcement element will be composed of a polymeric material, more usually being a different polymeric material than that of the tubular matrix. Preferably, the tubular matrix will be a polyamide polyether block copolymer, or other polymeric material having a hardness in the range from 20 D to 50 D. The axially reinforcement element will comprise a fiber or bundle of fibers composed of a high tensile strength polymer selected from the group consisting of polyimide, polytetrafluoroethylene (PTFE), and phenylenediamine polymers (such as Kevlar®, DuPont).

While the helical and axially reinforcement elements of the catheters of the present invention may be employed separately, it will be preferred to employ both reinforcement elements together in single catheter constructions.

According to a method of the present invention, reinforced catheter body portions may be fabricated by winding the polymeric reinforcement element in a generally helical pattern over a cylindrical mandrel, usually directly over the mandrel without any intermediate layers or structures. Usually, the helically wound reinforcement element and mandrel are then covered with a layer of polymeric material, and both the polymeric reinforcement element and the polymeric layer are composed of thermoplastics which will fuse together upon the subsequent application of heat and pressure. Heat and radially constrictive pressure are then applied in order to melt or fuse the two materials together. The reinforcement element and the polymeric layer will be composed of similar or the same thermoplastic materials having different hardnesses described above. In the exemplary case, both the reinforcement element and the polymeric layer will be composed of polyamide polyether block copolymers having the hardnesses set forth above. Heat and radially constrictive pressure are preferably applied by placing a heat shrink tube about the assembly of the polymeric layer, polymeric reinforcement element, and mandrel, and thereafter applying heat at a temperature sufficient to constrict the heat shrink tube and at least partially melt the thermoplastics so that the reinforcement elements fuse to the resulting tubular matrix.

DESCRIPTION OF THE PREFERRED EMBODIMENT

Figure 1:
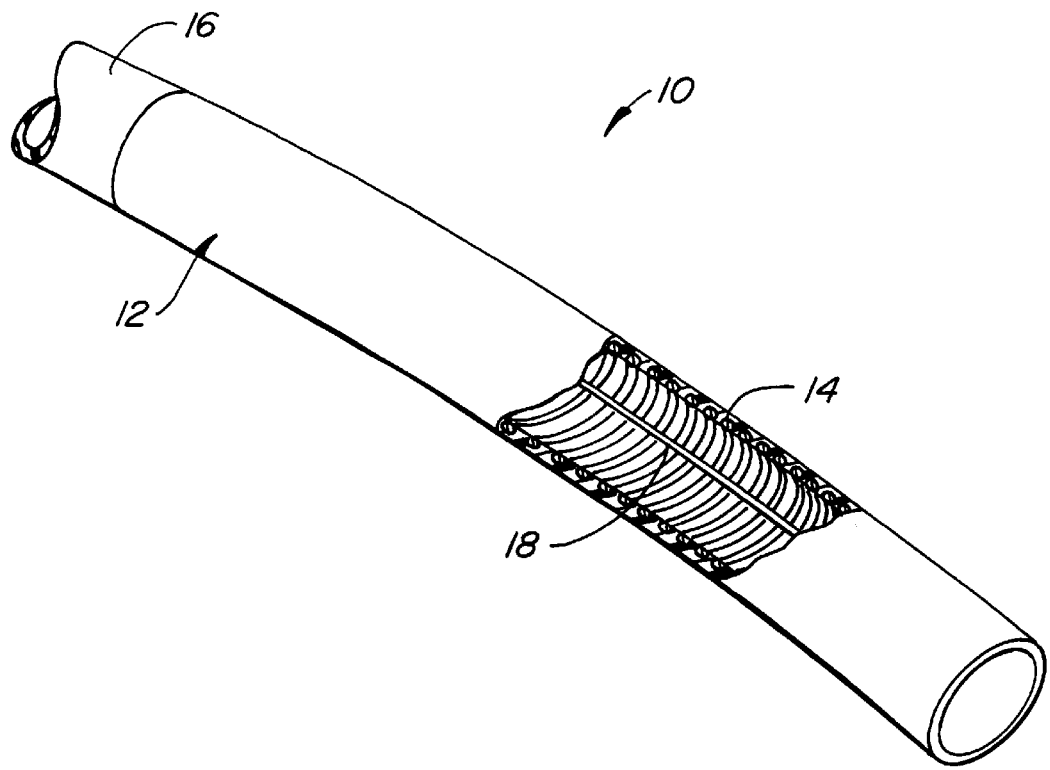
FIG. 1 is a perspective view of the distal end of a catheter having a reinforced tubular body segment constructed in accordance with the principles of the present invention, with a portion broken away.
Figure 2:
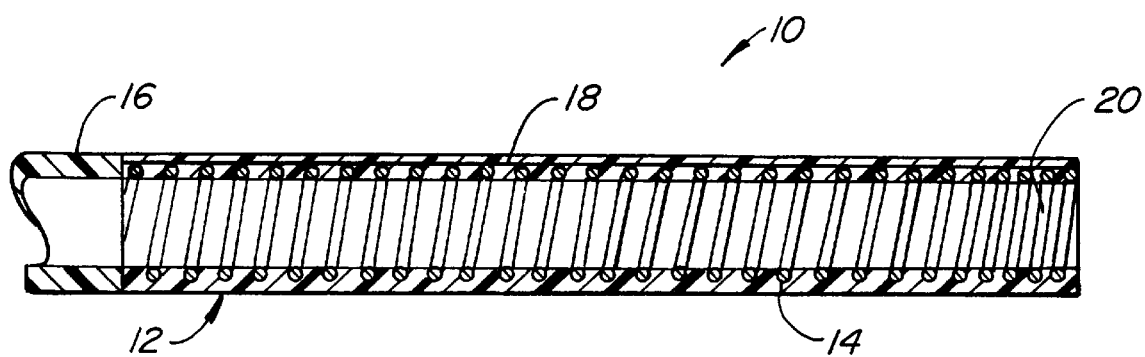
FIG. 2 is a side view of the distal end of the catheter of FIG. 1, shown in section.

Referring to FIGS. 1 and 2, a catheter 10 constructed in accordance with the principles of the present invention comprises a tubular body 12, wherein at least a portion of the body comprises a helical reinforcement element 14. In addition to the helically reinforced portion, catheter 10 also comprises a proximal portion 16 which is usually more rigid than the distal portion comprising the helical reinforcement element 14. Proximal portion 16 may itself be reinforced or free of reinforcement, and the entire catheter 10 may be configured to fulfill a variety of specific uses. For example, the catheter 10 may be intended as small diameter catheter for neurological diagnosis and intervention. In both cases, the reinforced portion of the catheter will comprise a highly flexible distal end, typically having a length in the range from 2 cm to 50 cm. In some cases, the distal segment may be sufficiently flexible so that the catheter 10 may be used as a flow directed catheter. In such both, the exterior and/or interior of the catheter may be coated with a hydrophilic material.

The catheter 10 further comprises an axial reinforcement element 18 which extends axially through the helically reinforced portion. The catheters according to the present invention may utilize the helical reinforcement elements and axial reinforcement elements separately or together, but will preferably employ both together in order to achieve both enhanced hoop strength (from the helical reinforcement element 14) and tensile strength (from the axial reinforcement segment 18).

As shown in FIGS. 1 and 2, the helical reinforcement element 14 is a small bead of a suitable polymeric material which is fused within surrounding matrix of polymeric material which comprises the tubular body. The polymeric material comprising the reinforcement bead 14 and the tubular matrix in which it is embedded may comprise a wide variety of thermoplastics. Suitable thermoplastics include polyamide polyether block copolymer, commercially available under the tradename (Pebax™), polyethylene, polyvinyl chloride (PVC), polytetrafluoroethylene (PTFE), and the like. The polymeric materials of the helical reinforcement element and the surrounding matrix may be the same or different, but will typically be the same material having a different hardness within the ranges set forth above. Particularly preferred is the use of an extruded bead of polyamide polyether block copolymer typically having a diameter in the range from 0.05 mm to 0.2 mm. The bead will be embedded and fused within a matrix of polyether polyamide block copolymer, which has a lower hardness, with particular ranges being set forth above.

The axial reinforcement element 18 will be composed of a material having a relatively high tensile strength typically above 200 KSI, preferably above 300 KSI. The material may be a metal, ceramic, or the like, but will preferably be a polymeric material, such as polyimide (Vectran™), polytetrafluoroethylene, phenylenediamine polymer (Kevlar®), or the like. The reinforcement element may be a single fiber or may be a bundle of fibers, e.g. a yarn, and will usually extend the entire length of the segment of the catheter body which is to be reinforced. In the embodiment of FIGS. 1 and 2, the axial reinforcement element 18 is coextensive with the length of the helical reinforcement element 14, but this is not necessarily the case for all embodiments.

Catheter 10 optionally comprises a radiopaque marker 20 at its distal tip. A marker 20 is shown as a coil of radiopaque material, such as platinum wire. It could also be a platinum ring, radiopaque doping, or the like.

Figure 3:
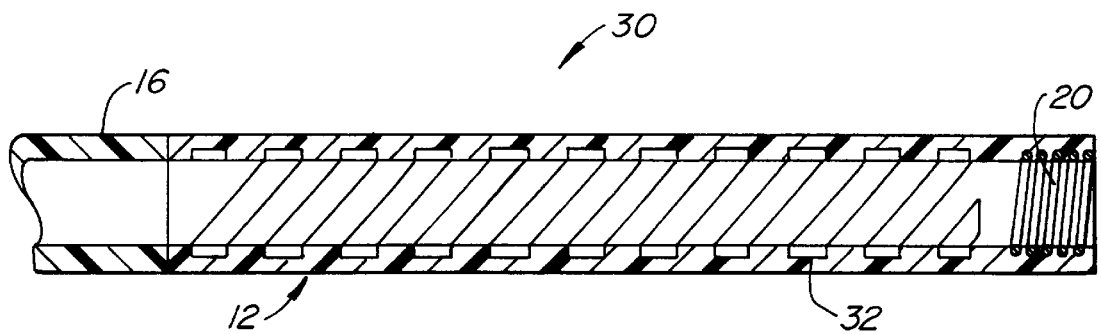
FIG. 3 is a side view of an alternative embodiment of the distal end of the catheter of FIG. 1, shown in section.

Referring now to FIG. 3, an alternative embodiment of the catheter of the present invention will be described. Catheter 30 comprises a helical reinforcement ribbon 32 and does not includes an axial reinforcement member. In other respects, the catheter 30 is identical to catheter 10 described above, and the remaining components have identical reference numerals. It will be appreciated that the helical reinforcement element could have a variety of other cross sections in addition to circular and rectangular (i.e. ribbon). The dimensions of the of the reinforcements, however, should generally be selected so that they may be entirely embedded within the wall thickness of the reinforced catheter section. While the inner surfaces of the reinforcement elements 14 and 32 may be exposed to the inner lumen of the catheter, the luminal surface will generally be smooth without ridges or protrubrances resulting from the presence of the reinforcement element. The smooth surface may be obtained by employing particular fabrication methods, as described below.

Figure 4:
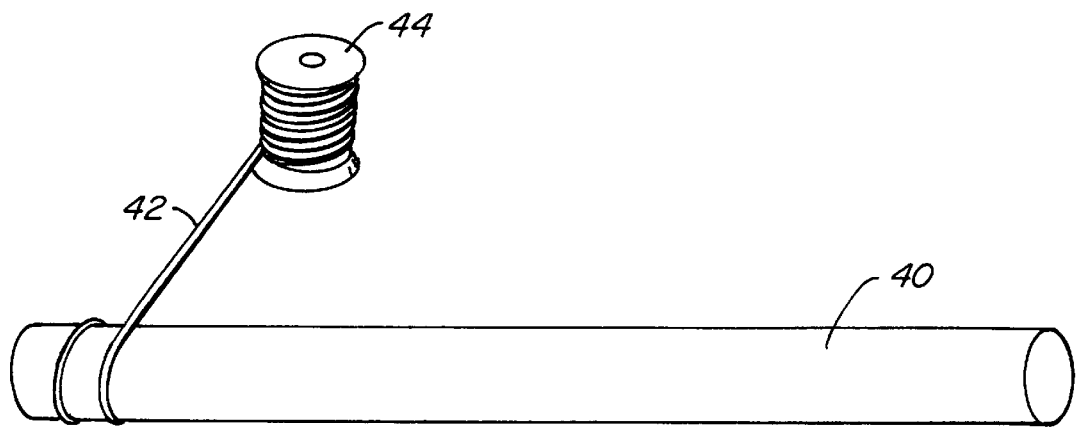
FIGS. 4 and 5 illustrate the catheter fabrication method of the present invention.
Figure 5:
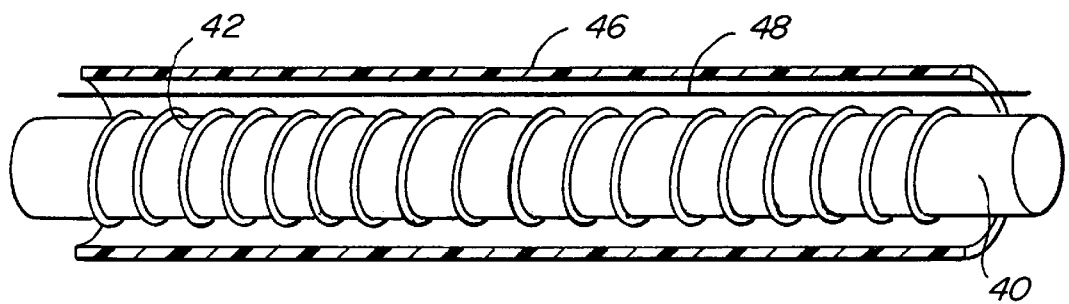

Referring now to FIGS. 4 and 5, catheter segments according to the method of the present invention may be fabricated on a cylindrical mandrel 40 having an outer diameter equal to the desired inner diameter of the catheter. A continuous length 42 of the desired reinforcement material is first wound onto the mandrel 40 in a conventional manner. The reinforcement material 42 will usually be a bead or ribbon of the desired polymer which has been previously extruded and wound onto a spool 44. The material 42 will be wound with a slight tension, and the diameter or width of the material 42 will be slightly drawn down as it is positioned over the mandrel. In the exemplary embodiment, the reinforcement material 42 will be a polyamide polyether block copolymer bead having a diameter of approximately 0.15 mm and a hardness of 72 D. Sufficient tension is applied to reduce the bead diameter to approximately 0.9 mm as it is laid onto the mandrel. The spacing between adjacent turns of the bead will be about 0.05 mm to 0.1 mm.

After the helical reinforcement 42 has been wound onto the mandrel 40, a layer 46 (FIG. 5) of polymeric matrix material will be placed over the helical reinforcement. Preferably, axial reinforcement element 48 is placed between the helical reinforcement 42 and the matrix layer 46. The thickness of the layer 46 will be selected so that the final thickness of the matrix, after melting as described below, will be 0.01 mm to 0.02 mm (where the overall tubular diameter is approximately 0.75 mm to 1 mm). The polymeric material 46 will also be a polyamide polyether copolymer, but will have a hardness of about 35 D, thus being substantially softer than the beading material which comprises the helical reinforcement element.

The polymeric layer 46 is melted and fused into the helical reinforcement bead 42, optionally entrapping axial reinforcement layer 48 therebetween, by placing a shrink wrap tube, such as a polyethylene or fluoropolymer, tube thereover. The entire assembly is then placed in an oven and heated to a temperature sufficient to constrict the shrink wrap tube and melt the thermoplastic materials which form the reinforcement bead 42 and polymeric layer 46. Thus, the outer surface of mandrel 40 will define the smooth interior surface of the resulting lumen of the catheter. Usually, the axial reinforcement element 48 will not be a thermoplastic and will not be melted into the resulting structure. The axial reinforcement member 48, however, will be firmly entrapped between the helical reinforcement element 42 and the polymeric matrix which results from melting of the layer 46.

After cooling, the shrink wrap tube may be removed from the assembly, and the resulting catheter section removed from the mandrel. After trimming the ends as desired, the catheter section may optionally be joined to other catheter sections in a conventional manner. Heat or adhesive bonding may be used for forming butt joints between adjacent catheter sections. Adjacent catheter sections may have quite different mechanical properties and/or physical dimensions.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising a tubular body, wherein at least a portion of the tubular body comprises a helical reinforcement element composed of a first polymeric material embedded in a tubular matrix composed of a second polymeric material which is softer than the first polymeric material, wherein the reinforcement element is fused to the polymeric matrix, wherein the risk of delamination is reduced.

2. A catheter as in claim 1, wherein the portion of the tubular body comprising the reinforcement element has a wall thickness in the range from 0.05 mm to 0.35 mm.

3. A catheter as in claim 2 wherein the reinforcement element is disposed adjacent an inner surface of the tubular wall.

4. A catheter as in claim 2, wherein the helical reinforcement element has a generally circular cross-section with a diameter in the range from 0.02 mm to 0.3 mm.

5. A catheter as in claim 2, wherein the helical reinforcement element is a ribbon having a width in the range from 0.05 mm to 0.5 mm and a thickness in the range from 0.025 mm to 0.15 mm.

6. A catheter as in claim 2, wherein the portion of the tubular body comprising the helical reinforcement element has an outer diameter in the range from 0.3 mm to 2 mm and an inner lumen diameter from 0.2 mm to 0.8 mm.

7. A catheter as in claim 6, wherein the catheter has a length in the range from 40 cm to 200 cm and the reinforced portion has a length in the range from 2 cm to 50 cm.

8. A catheter as in claim 7 wherein successive turns of the helical reinforcement element are spaced-apart by a distance in the range from 0.025 mm to 1 mm and the helical reinforcement element has a pitch in the range from 10 turns/cm to 400 turns/cm.

9. A catheter as in claim 1, further comprising an axial reinforcement element extending through at least a portion of the helically reinforced portion of the tubular body.

10. A catheter as in claim 9, wherein the axial reinforcement element extends through the entire length of the reinforced portion of the tubular body.

11. A catheter as in claim 10, wherein the axial reinforcement element is composed of a polymeric material.

12. A catheter as in claim 11, wherein the polymeric material of the axial reinforcement element is different than the polymeric matrix material.

13. A catheter as in claim 12, wherein the polymer of the axial reinforcement element is selected from the group consisting of polyimide, polytetrafluoroethylene, and phenylenediamine polymer.

14. A catheter as in claim 1, wherein the first polymeric material has a hardness in the range from 40 D to 80 D and the second polymeric material has a hardness in the range from 20 A to 50 D.

15. A catheter as in claim 14, wherein the first polymeric material and the second polymeric material are the same type of polymer.

16. A catheter as in claim 15, wherein the first polymeric material comprises polyamide polyether block copolymer having a hardness in the range from 40 D to 72 D and wherein the second polymeric material comprises polyamide polyether block copolymer having a hardness in the range from 25 D to 40 D.

17. A catheter as in claim 1, wherein the tubular body has a proximal end, a distal end, and at least one additional portion free from the helical reinforcement element.

18. A catheter as in claim 17, wherein the portion of the catheter body having the helical reinforcement element is distal to the portion which is free from the helical reinforcement element.

19. A catheter comprising a tubular body, wherein at least a portion of the tubular body comprises a helical reinforcement element composed of a first polymeric material embedded in a tubular matrix composed of a second polymeric material which is softer than the first polymeric material, wherein the reinforcement element is fused to the polymeric matrix, wherein the first polymeric material and the second polymeric material are the same type of polymer.

20. A catheter as in claim 19, wherein the portion of the tubular body comprising the reinforcement element has a wall thickness in the range from 0.05 mm to 0.35 mm.

21. A catheter as in claim 20, wherein the helical reinforcement element has a generally circular cross-section with a diameter in the range from 0.02 mm to 0.3 mm.

22. A catheter as in claim 20, wherein the helical reinforcement element is a ribbon having a width in the range from 0.05 mm to 0.5 mm and a thickness in the range from 0.025 mm to 0.15 mm.

23. A catheter as in claim 22 wherein the reinforcement element is disposed adjacent an inner surface of the tubular wall.

24. A catheter as in claim 20, wherein the portion of the tubular body comprising the helical reinforcement element has an outer diameter in the range from 0.3 mm to 2 mm and an inner lumen diameter from 0.2 mm to 0.8 mm.

25. A catheter as in claim 24, wherein the catheter has a length in the range from 40 cm to 200 cm and the reinforced portion has a length in the range from 2 cm to 50 cm.

26. A catheter as in claim 25 wherein successive turns of the helical reinforcement element are spaced-apart by a distance in the range from 0.025 mm to 1 mm and the helical reinforcement element has a pitch in the range from 10 turns/cm to 400 turns/cm.

27. A catheter as in claim 19, further comprising an axial reinforcement element extending through at least a portion of the helically reinforced portion of the tubular body.

28. A catheter as in claim 27, wherein the axial reinforcement element extends through the entire length of the reinforced portion of the tubular body.

29. A catheter as in claim 28, wherein the axial reinforcement element is composed of a polymeric material.

30. A catheter as in claim 29, wherein the polymeric material of the axial reinforcement element is different than the polymeric matrix material.

31. A catheter as in claim 30, wherein the polymer of the axial reinforcement element is selected from the group consisting of polyimide, polytetrafluoroethylene, and phenylenediamine polymer.

32. A catheter as in claim 19, wherein the tubular body has a proximal end, a distal end, and at least one additional portion free from the helical reinforcement element.

33. A catheter as in claim 32, wherein the portion of the catheter body having the helical reinforcement element is distal to the portion which is free from the helical reinforcement element.

34. A catheter as in claim 19, wherein the first polymeric material has a hardness in the range from 40 D to 80 D and the second polymeric material has a hardness in the range from 20 A to 50 D.

35. A catheter as in claim 19, wherein the first polymeric material comprises polyamide polyether block copolymer having a hardness in the range from 40 D to 72 D and wherein the second polymeric material comprises polyamide polyether block copolymer having a hardness in the range from 25 D to 40 D.

36. A catheter comprising a tubular body, wherein at least a portion of the tubular body comprises a tubular matrix composed of a polymeric material having a hardness less than 50 D, a helical reinforcement element composed of a polymeric material fused to the tubular body, and an axial reinforcement element disposed axially within said portion, wherein said axial reinforcement element has a high tensile strength and is composed of a material different than that of the helical reinforcement element.

37. A catheter as in claim 36, wherein the tubular matrix polymeric material has a hardness in the range from 20 A to 50 D and the helical reinforcement element polymeric material has a harness in the range from 40 D to 80 D.

38. A catheter as in claim 37, wherein the tubular matrix polymeric material and the helical reinforcement element polymeric material are the same type of polymer.

39. A catheter as in claim 38, wherein the tubular matrix polymeric material comprises polyamide polyether block copolymer having a hardness in the range from 25 D to 40 D and wherein the helical reinforcement element polymeric material comprises polyamide polyether block copolymer having a hardness in the range from 40 D to 72 D.

40. A catheter as in claim 36, wherein the axial reinforcement element is composed of a polymeric material.

41. A catheter as in claim 40, wherein the polymer of the axial reinforcement element is selected from the group consisting of polyimide, polytetrafluoroethylene, and phenylenediamine polymer.

42. A catheter as in claim 36, wherein the helical reinforcement element is composed of a polymeric material.

43. A catheter as in claim 36, wherein the portion of the tubular body comprising the axial reinforcement element has an outer diameter in the range from 0.3 mm to 2 mm and an inner lumen diameter from 0.2 mm to 1.5 mm.

44. A catheter as in claim 36, wherein the catheter has a length in the range from 40 cm to 200 cm and the reinforced portion has a length in the range from 2 cm to 50 cm.

45. A catheter as in claim 36, wherein the tubular body has a proximal end, a distal end, and at least one additional portion free from the axial reinforcement element.

46. A catheter as in claim 45, wherein the portion of the catheter body having the axial reinforcement element is distal to the portion which is free from the helical reinforcement element.

* * * * *